United States Patent [19]

Batz et al.

[11] Patent Number: 4,980,299

[45] Date of Patent: Dec. 25, 1990

[54] CARRIER FOR COATING WITH IMMUNOLOGICALLY-ACTIVE MATERIAL

[75] Inventors: Hans-Georg Batz, Tutzing; Herbert Hopp, Weilheim; Klaus Stellner, Bernried, all of Fed. Rep. of Germany

[73] Assignee: Boehringer Mannheim GmbH, Mannheim, Fed. Rep. of Germany

[21] Appl. No.: 129,420

[22] Filed: Nov. 25, 1987

Related U.S. Application Data

[63] Continuation of Ser. No. 612,564, May 21, 1984, abandoned.

[30] Foreign Application Priority Data

May 19, 1983 [DE] Fed. Rep. of Germany ....... 3318184

[51] Int. Cl.$^5$ ................. G01N 33/544; G01N 33/545
[52] U.S. Cl. ........................................ 436/531; 427/2; 436/533; 436/807; 524/565; 524/582; 524/579
[58] Field of Search ................. 436/531, 533, 85, 807; 425/550; 264/DIG. 16; 524/565, 582, 579; 427/2

[56] References Cited

U.S. PATENT DOCUMENTS

| | | |
|---|---|---|
| 3,646,346 | 2/1972 | Catt ..................................... 436/531 |
| 3,790,663 | 2/1974 | Garrison et al. .................... 436/531 |
| 4,118,349 | 10/1978 | Bonacker et al. .................. 525/54.1 |
| 4,258,001 | 3/1981 | Pierce et al. ............................ 435/7 |

OTHER PUBLICATIONS

Golding, B., (1959), Polymers and Resins Their Chemistry & Chemical Engineering, Van Nostrand Company, Inc., Princeton, N.J., pp. 130–145, 398–418, 512–519, and 590–592.

Primary Examiner—Sam Rosen
Assistant Examiner—David A. Saunders
Attorney, Agent, or Firm—Felfe & Lynch

[57] ABSTRACT

The present invention provides a carrier for coating with immunologically-active material, wherein it consists of an injection molded synthetic resin with a content of adjuvant and additional materials of less than 1% by weight. The present invention also provides a carrier coated with immunologically-active material, wherein the carrier consists of synthetic resin with a content of adjuvant and additional materials of less than 1% by weight.

15 Claims, No Drawings

CARRIER FOR COATING WITH IMMUNOLOGICALLY-ACTIVE MATERIAL

This application is a continuation, of application Ser. No. 612,564, filed May 21, 1984, now abandoned.

The present invention is concerned with a carrier for coating with immunologically-active material.

In immunology, synthetic resin articles are frequently used, on the surfaces of which are bound immunological material. By means of the use of such coated synthetic resin articles, the separation of the bound from the non-bound portions usually necessary in immunological test processes is simplified. Thus, for example, radioimmunoassays and enzyme immunoassays for the determination of an antigen or hapten are carried out by introducing a solution containing the antigen or hapten to be determined into a synthetic resin vessel, the inner surface of which is coated with antibodies directed against the antigen or hapten. Into the vessel there is also introduced a known amount of the antigen or hapten to be determined, which is marked in a characteristic way, for example with an enzyme or a radioactive material. The antigen/hapten to be determined and the marked antigen/hapten compete for the antibody binding sites, an equilibrium being obtained between the portion of antigen or hapten bound to the antibodies and the free portion thereof remaining in the solution. The solution containing free portion is removed from the vessel. The portion bound by the antibodies remains adhering to the wall of the vessel and can there be detected.

In order to be able to carry out several determinations comparable with one another, it is necessary that the coating of the synthetic resin vessels with the appropriate antibody, if an antigen or hapten is to be detected, or with an antigen or hapten, if an antibody is to be detected, takes place with a great degree of uniformity. If the coating thickness differs from one vessel to another, then this has an effect on the very sensitive immunological reaction, the measurement results being falsified.

The most varied kinds of carrier are commercially available in the form of plates, spheres, strips, rodlets or reagent tubes made from the most varied kinds of synthetic resins. If these commercially-available carriers are coated with an immunological material, then the coating thickness varies and thus the measurement results obtained in the case of an immunological reaction also vary considerably. Variation coefficients are observed which generally cannot be accepted in the case of the highly sensitive immunotests. In Clin. Chem., 26, 741-744/1980, for example, there are given variation coefficients of from 5.2 to 29.5% for microtitre plates made of polystyrene.

Many attempts have been made to improve the variation coefficients. Thus, for example, according to Federal Republic of Germany Patent Specification No. 25 44 366, an attempt has been made to strengthen and make uniform the binding of the immunological material on to the carrier surface by cross-linking with glutardialdehyde. Also by means of the variation of the coating times and with the help of a precoating or subsequent coating, attempts have been made to produce a uniform coating thickness (cf. Biochemica et Biophysica Acta, 492, 399-407/1977). Furthermore, in J. Immunol. Methods, 23, 23-28/1978, as well as 47, 121-124/1981, it is reported that by the addition of a detergent (Tween 20 or Tween 80), an increased adsorption of the immunological material on the carrier surface is achieved. A further attempt to make the coating thickness uniform consisted in covalently binding the immunological material to the carrier surface, this principle being, for example, described and claimed in Federal Republic of Germany Patent Specification No. 27 38 138.

All these endeavours admittedly resulted in an increased binding of the antibody or antigen on to the synthetic resin surface and also led to an improvement of the variation coefficients. The previously available commercial products have variation coefficients of from 5 to 10%. Thus, it has not been possible to achieve a uniform loading thickness to such an extent that the measurement results obtained with these materials are satisfactory in practice.

It is an object of the present invention to provide a synthetic resin carrier which can be uniformly coated with immunologically-active material.

Thus, according to the present invention, there is provided a carrier for coating with immunologicallyactive material, wherein it consists of synthetic resin with a content of adjuvant and additional materials of less than 1% by weight.

The synthetic resins previously used for the production of such synthetic resin articles usually contained, depending upon the synthetic resin, from 1 to 50% by weight of adjuvant or additional materials. Such adjuvant or additional materials are usually stabilisers, lubricants, plasticisers, separating agents, pigments, filling materials and the like. Luran, a synthetic resin frequently used for producing synthetic resin carriers, contains, for example, 1 to 5% by weight of such materials and polyvinyl chloride even up to 50% by weight of such materials.

As synthetic resins, according to the present invention, there can, in principle, be used all synthetic resins which are suitable for the production of synthetic resin objects by injection moulding processes. For the production of synthetic resin carriers according to the present invention, it has proved to be especially advantageous to use polystyrene, Luran, polypropylene and polyvinyl chloride. It is merely necessary to ensure that only those synthetic resin batches are used, the adjuvant and additional material content of which is less than 1% by weight. Preferably, only Luran batches are employed with an adjuvant and additional material content of less than 0.2% by weight or polystyrene batches with an adjuvant and additional material content of less than 0.05% by weight.

The synthetic resin carriers can be produced in any desired shape. Usually, they are in the form of plates, spheres, reagent tubes or also strips and rodlets.

The synthetic resin carriers are usually produced by injection molding processes, using parameters known to one skilled in the art. The parameters will vary, depending upon the synthetic resin used and the actual molding device.

Usually the pressure is selected within the range of from 100 to 250 bar and the injection temperature within the range of from 190° to 280° C. However, care is to be taken that the selected pressure and the selected temperature during the injection moulding process are kept within narrow limits. The pressure should vary not more than ±2 bar and the temperature not more than ±2° C. Furthermore, in order to obtain optimum results, it is necessary that the surface of the injection moulding body is very homogeneous and does not have any unevennesses and that the injection moulding body is uniformly cooled to a temperature, which is preferably within the range of from 20° and 40° C. and does not vary more than ±1° C.

The synthetic resin carriers according to the present invention can be coated in known manner with immunologically-active material, i.e. with antibodies, antigens and haptens. For this purpose, a solution of the immunologically-active material is allowed to act upon the synthetic resin carrier for a time sufficient for loading. As solvent, there is generally used water which contains an appropriate buffer. The pH value of the solution is not critical and has to be selected essentially in dependence of the coating material. The pH value is usually in the range of from 5 to 8, preferably in the neutral range. For the complete loading of the synthetic resin carrier, in general it suffices to use an action time of 12 to 24 hours. The temperature can be selected within the range of from 15° to 30° C. However, during the incubation, it should preferably vary only by ±0.5° C.

It has proved advantageous to follow the actual loading by a subsequent loading in which the synthetic resin carrier coated with the immunological material is exposed to a solution which contains an appropriate salt, for example sodium chloride, and a stabilising agent, for example bovine serum albumin. For the subsequent loading, there suffices a time of from 10 to 120 minutes and preferably of from 15 to 60 minutes.

The test tubes or the like so coated are packed in a sterile manner and can be made commercially available as such. They are stable for several months and can be used in usual immunotest processes. They display a variation coefficient of <5%. The test results obtained with the synthetic resin carriers according to the present invention display a distinctly smaller breadth of variation than the results which have been obtained in an analogous manner with the previously used synthetic resin carriers.

The following Example is given for the purpose of illustrating the present invention:

EXAMPLE

ANTIBODY SOLUTION 952 g. Sodium dihydrogen phosphate monohydrate of analytical purity grade are dissolved in 5 litres of water and adjusted to pH 7.1 with 5N aqueous sodium hydroxide solution. This solution is stirred into 165 litres of water. If necessary, the pH value is adjusted to 7.1 to 7.4 by the addition of 5N aqueous sodium hydroxide solution.

Into 500 ml. of this buffer solution are introduced 8.5 ml. of antiserum and 8.5 ml. of bovine serum albumin solution (1.5 g. per 25 ml. of water) and stirred for 30 minutes. The antiserum solution thus obtained is made up with buffer to 2 litres and again stirred for 30 minutes. This solution is combined with the remaining buffer solution and again stirred for 30 minutes.

LOADING 100,000 Tubelets made of polystyrene 168N K21, containing <0.9% by weight of additional materials are each filled with 1.5 ml. ±5%. The antibody solution is allowed to act for 16 to 18 hours at 20°±0.5° C. on the tubelets and thereafter sucked off.

SUBSEQUENT LOADING

First, 1710 g. sodium chloride of analytical purity grade and 570 g. bovine serum albumin Type II are dissolved in 180 litres of water, stirred for 30 minutes and left to stand overnight at ambient temperature. The tubelets loaded with antibody are each filled with 1.7 ml.±5% of the above-described subsequent loading solution. The solution is allowed to act for 15 to 30 minutes on the tubelets. Thereafter, the tubelets are emptied, rinsed out twice and dried in a drying cabinet for 14 to 16 hours.

DETERMINATION OF THE VARIATION COEFFICIENTS

From each subunit ($\hat{=}$ 10,000 tubelets) of a loading batch, there are randomly selected 100 tubelets ($\hat{=}$1%) and these are recorded. The tubelets are divided into two groups, each containing 50 tubelets, for a first and second test series. With the tubelets of the first test series, there is carried out a conventional enzyme immune test. After the substrate reaction has taken place, the solutions are measured on a photometer against substrate solution in a flowthrough cuvette and the extinction values obtained are recorded.

From the individual extinctions $E_1$ to $E_{50}$, there is calculated the average extinction $\bar{E}$. The standard deviation S is determined according to equation (1):

$$S = \frac{\sqrt{(E_1 - \bar{E})^2 + (E_2 - \bar{E})^2 + \ldots (E_{50} - \bar{E})^2}}{49} \quad (1)$$

and the variation coefficient VC according to equation (2):

$$VC = S/\bar{E} \quad (2)$$

For the above-described tubelets produced from polystyrene 168N K21, there is obtained, in this way, a variation coefficient VC of 2.8%.

It will be understood that the specification and examples are illustrative but not limitative of the present invention and that other embodiments within the spirit and scope of the invention will suggest themselves to those skilled in the art.

What is claimed is:

1. Process for producing a carrier coated with an immunologically active material having a variation coefficient of less than 5%, comprising:
   injection molding a synthetic resin having a content of adjuvant or additional materials selected from the group consisting of stabilizers, lubricants, plasticisers, separating agents, pigments and filling materials of less than 1% by weight at a temperature of from 190° to 280° C., said temperature being regulated so as not to very by more of less than 2° C.,
   cooling said injection molded synthetic resin at a temperature of from 20° C., to 40° C., wherein said temperature does not vary by more or less than 1° C.,
   loading said injection molded synthetic resin by incubating it with a solution of an immunologically active material, and drying the loaded injection molded synthetic resin.

2. Process of claim 1, wherein said synthetic resin is injection molded at a pressure of from 100 to lb 250 bar, wherein said pressure is regulated to vary by not more or less than 2 bar.

3. The process of claim 1, wherein said injection molded synthetic resin and said solution of immunologically active material are incubated at a temperature of from 15° C. to 30° C., said incubating temperature being regulated so as to vary by not more or less than 0.5° C.

4. The process of claim 1, wherein said injection molded synthetic resin and said solution of immunologically active material are incubated for a period of from 12 to 24 hours.

5. The process of claim 1, wherein said solution of immunologically active material has a pH of from 5 to 8.

6. The process of claim 1, comprising drying said loaded injection molded synthetic resin for from 14 to 16 hours.

7. The process of claim 1 wherein the loading step comprises applying a solution of the immunologically active material to the injected molded synthetic resin while maintaining a temperature in the range of 15° C., to 30° C., with a variation of ±0.5° C., for 12 to 24 hours and thereafter exposing the resin to a salt containing stabilizing solution for 10 to 120 minutes.

8. The process of claim 1 wherein the synthetic resin is selected from the group consisting of polystyrene, Luran, polypropylene and polyvinyl chloride.

9. The process of claim 8 wherein the synthetic resin is Luran with a content of adjuvant and additional materials of less than 0.2% by weight.

10. The process of claim 8 wherein the synthetic resin is polystyrene with a content of adjuvant and additional materials of less than 0.05% by weight.

11. Method for determining an analtye in a sample comprising contacting a liquid sample with an immunologically active material prepared in accordance with the process of claim 1, wherein said immunologically active material reacts with said analyte to form a complex thereby, and determining said complex as a determination of said analyte.

12. Immunologically active injection molded synthetic resin carrier prepared by the process of claim 1.

13. The carrier of claim 12, wherein the synthetic resin used is selected from the group consisting of polystyrene, Luran, polypropylene and polyvinyl chloride.

14. The carrier of claim 13 wherein the synthetic resin is polystyrene with a content of adjuvant and additional materials of less than 0.5% by weight.

15. The carrier of claim 12 wherein the synthetic resin is Luran with a content of adjuvant and additional materials of less than 0.02% by weight.

* * * * *